(12) United States Patent
Moshe (10) Patent No.: US 6,697,510 B2
(45) Date of Patent: Feb. 24, 2004

(54) METHOD FOR GENERATING INTRA-PARTICLE CRYSTALLOGRAPHIC PARAMETER MAPS AND HISTOGRAMS OF A CHEMICALLY PURE CRYSTALLINE PARTICULATE SUBSTANCE

(75) Inventor: Danny S. Moshe, Kiryat Ono (IL)

(73) Assignee: Green Vision Systems Ltd., Tel Aviv (IL)

( * ) Notice: Subject to any disclaimer, the term of this patent is extended or adjusted under 35 U.S.C. 154(b) by 0 days.

(21) Appl. No.: 10/255,719

(22) Filed: Sep. 27, 2002

(65) Prior Publication Data

US 2003/0083826 A1 May 1, 2003

Related U.S. Application Data

(63) Continuation-in-part of application No. PCT/IL01/01110, filed on Dec. 2, 2001, and a continuation-in-part of application No. PCT/IL01/00366, filed on Apr. 19, 2001.
(60) Provisional application No. 60/324,913, filed on Sep. 27, 2001.

(51) Int. Cl.[7] .................................................. G06K 9/00
(52) U.S. Cl. ........................ 382/133; 382/128; 382/170; 382/167; 382/134; 702/27; 356/300
(58) Field of Search ................................ 382/133, 128, 382/134, 255, 168, 170; 377/10; 356/300, 317; 702/27

(56) References Cited

U.S. PATENT DOCUMENTS

| | | | | | |
|---|---|---|---|---|---|
| 5,568,571 A | * | 10/1996 | Willis et al. | ................ | 382/254 |
| 6,137,899 A | * | 10/2000 | Lee et al. | ................... | 382/133 |
| 6,208,749 B1 | * | 3/2001 | Gutkowicz-Krusin et al. | ............... | 382/128 |
| 6,584,413 B1 | * | 6/2003 | Keenan et al. | ................ | 702/28 |
| 2002/0097388 A1 | * | 7/2002 | Raz | ............................. | 356/39 |
| 2003/0049867 A1 | * | 3/2003 | Selifonov et al. | ........... | 436/518 |

* cited by examiner

Primary Examiner—Timothy M. Johnson
Assistant Examiner—Barry Choobin
(74) Attorney, Agent, or Firm—G. E. Ehrlich Ltd.

(57) ABSTRACT

Method for generating intra-particle crystallographic parameter maps and histograms of a chemically pure crystalline particulate substance. Spectral imaging, in general, and focus-fusion multi-layer spectral imaging, in particular, combined with pattern recognition classification analysis are performed on individual particles for forming sets of single-particle spectral fingerprint data, characterized by single-particle spectral fingerprint spectra. Spectral shifts are identified in the single-particle spectral fingerprint data, for forming intra-particle crystallographic region groups each featuring sub-sets of intra-particle spectral fingerprint pattern data, where selected data elements in each sub-set are shifted relative to corresponding data elements in remaining sub-sets in the same intra-particle crystallographic region group. Each intra-particle crystallographic region group is associated with different crystallographic parameters of crystal type and crystal class, for forming intra-particle crystallographic parameter data, which is used for generating intra-particle crystallographic parameter maps and histograms of the chemically pure crystalline particulate substance throughout an entire multi-particle sample.

52 Claims, 4 Drawing Sheets

METHOD FOR GENERATING INTRA-PARTICLE CRYSTALLOGRAPHIC PARAMETER MAPS AND HISTOGRAMS OF A CHEMICALLY PURE CRYSTALLINE PARTICULATE SUBSTANCE

This claims the benefit of priority of U.S. Provisional Patent Application No. 60/324,913, filed Sep. 27, 2001, entitled: "Method For Generating Intra-particle Crystallographic Parameter Maps And Histograms Of A Chemically Pure Crystalline Particulate Substance", the specification of which is herein incorporated by reference.

This is also a Continuation-in-Part of PCT International Patent Application No. PCT/IL01/01110, filed Dec. 2, 2001, entitled: "Method For In-situ Focus-fusion Multi-layer Spectral Imaging And Analysis Of Particulate Samples", and a Continuation-in-Part of PCT International Patent Application No. PCT/IL01/00366, filed Apr. 19, 2001, entitled: "Method For Generating Intra-particle Morphological Concentration/Density Maps And Histograms Of A Chemically Pure Particulate Substance", the specifications of which are herein incorporated by reference.

FIELD AND BACKGROUND OF THE INVENTION

The present invention relates to a spectral imaging method for determining physicochemical properties and characteristics of a crystalline particulate substance, and more particularly, to a method for generating intra-particle crystallographic parameter maps and histograms of a chemically pure crystalline particulate substance, by spectral imaging of individual particles of the chemically pure crystalline particulate substance and analyzing the spectral images using pattern recognition classification analysis.

In the field of commercial handling, processing, and manufacturing, of crystalline particulate substances, including analysis and control thereof, especially as applied in the biopharmaceutical industry, there is on-going interest, resources, and activities, being devoted to techniques for measuring, determining, and analyzing, physicochemical data and information relating to crystallographic properties, characteristics, and parameters, of crystalline particulate substances, in general, and of chemically pure crystalline particulate substances, in particular.

In the highly regulated biopharmaceutical industry, an important stage during research and development of a new therapeutic product such as a natural or synthetic drug, high performance chemical, or, micro-organism, featuring at least one chemically pure crystalline particulate substance either in the raw material(s) and/or in the eventual finished pharmaceutical product formulated as a tablet capsule, caplet, or loose powder, involves extensive and well documented laboratory analytical testing of the physicochemical properties and characteristics of each chemically pure crystalline particulate substance. Analogous, but less stringent activities are also performed in the regulated food and beverage industries, regarding research and development of a new food or beverage product such as a natural or synthetic food or beverage ingredient, additive, high performance chemical, or, micro-organism, functioning as a flavor, a preservative, or, a consistency enhancer, featuring at least one chemically pure crystalline particulate substance either in the raw material(s) and/or in the eventual finished food or beverage product formulated as a stand alone compact or loose powder, or, as a compact or loose powder as part of another food or beverage product.

In a crystalline solid, herein, referred to as a crystalline particulate substance, to be distinguished from noncrystalline substances such as liquids and amorphous solids or amorphous particulate substances, structurally, the constituent particles, compounds, atoms, molecules, or ions, are arranged in an orderly, repetitive pattern or crystal structure in three dimensions. Herein, the term 'chemically pure crystalline particulate substance' refers to a crystalline particulate substance featuring a plurality of crystalline particles each composed of at least one chemically pure individual chemical compound, where the chemically pure crystalline particulate substance is typically heterogeneous with respect to morphological or geometrical distribution and/or with respect to frequency distribution of physicochemical properties and characteristics, such as concentration, density, particle size, particle geometry; particle shape, particle porosity, and crystallographic parameters of crystal type and crystal class, of the at least one chemically pure individual compound throughout a given sized sample of the chemically pure crystalline particulate substance.

In the biopharmaceutical industry, information about the physicochemical properties and characteristics of each chemically pure crystalline particulate substance are needed in a later stage for performing pharmacodynamical studies, involving metabolic and efficacy studies of the therapeutic product when ingested by an animal or human during pre-clinical and clinical studies. Metabolic information about the therapeutic product is needed for designing and evaluating efficacy studies, where the effectiveness of the therapeutic product for performing the indicated therapeutic function in a subject is measured. Ultimately, information and data from the efficacy studies are used for establishing the final formulation and recommended dosage levels of the new therapeutic product, for large scale dispensing to the consumer market. Correspondingly, data and information about the final formulation are used for establishing standardized quality control parameters and criteria for full-scale manufacturing of the new therapeutic product. Again, analogous, but less stringent activities are also performed in the regulated food and beverage industries, regarding each chemically pure crystalline particulate substance eventually ending up in a new food or beverage product, for large scale distribution to the consumer market.

Full-scale manufacturing of such a new or current, therapeutic, or, food or beverage, product, involves extensive and well documented standardized quality control testing of each chemically pure crystalline particulate raw material and/or each chemically pure crystalline particulate finished product, according to established quality control and quality assurance parameters and criteria. Similar to the research and development stages of such a product, this involves laboratory analytical testing and classification of the physicochemical properties and characteristics of each chemically pure crystalline particulate substance comprising the therapeutic, or, food or beverage, product.

Laboratory analytical testing of such a chemically pure crystalline particulate substance, during research and development stages or during routine finished product quality control testing, typically includes measuring and determining physicochemical properties and characteristics, such as concentration, density, particle size, particle geometry, particle shape, particle porosity, and/or crystallographic parameters, of a sample of the chemically pure crystalline particulate substance, in a statistically meaningful manner. Typically, such laboratory testing also includes measuring and determining dissolution properties of each applicable or selected chemically pure crystalline particulate substance. Dissolution testing provides data and information about the kinetics and thermodynamics of dissolution of a given chemically pure crystalline particulate substance in a variety of solvents. As indicated above, in the biopharmaceutical industry, such detailed information about the physicochemical properties and characteristics of each chemically pure crystalline particulate substance is valuable and used for either understanding, classifying, or quality control testing pharmacodynamical behavior of the therapeutic product.

It is well known in the field of physical chemistry of crystalline particulate matter, that dissolution properties and behavior of a crystalline particle, and therefore, of a sample of a crystalline particulate substance featuring a plurality of crystalline particles, in a liquid medium, either in-vitro or in-vivo, are, in varying degrees, related to and functions of morphological distribution and/or frequency distribution of physicochemical properties and characteristics, such as concentration, density, particle size, particle geometry, particle shape, particle porosity, and crystallographic parameters of crystal type and crystal class, of the crystalline particulate substance. Thus, measuring and determining data and information about the crystalline particle physicochemical properties and characteristics, are useful for highly accurately and reproducibly determining, understanding, classifying, and testing dissolution properties and behavior of the crystalline particulate substance. This relationship is clearly applicable to laboratory analytical testing of chemically pure crystalline particulate substances extensively performed by the biopharmaceutical, and, food and beverage industries, as described above.

There are extensive prior art methods, devices, and systems, relating to accurately and reproducibly measuring and determining physicochemical properties and characteristics of particulate substances, which are applicable to crystalline particulate substances, where these are typically based on imaging the particulate substance. Spectral imaging is currently a widely used technique for imaging particles. In spectral imaging, a particulate substance is affected in a way, for example, excitation by incident electromagnetic radiation, such as ultraviolet light upon the substance, which causes the substance to emit light featuring an emission spectra. Emitted light is recorded by an instrument such as a scanning interferometer that generates a set of interferogram images, which in turn are used to produce a spectral image, also referred to as a cube image, of the substance. Each cube (spectral) image is a three dimensional data set of voxels (volume of pixels) in which two dimensions are spatial coordinates or position, (x, y), in the substance and the third dimension is the wavelength, ($\lambda$), of the imaged (emitted) light of the substance, such that coordinates of each voxel in a spectral image or cube image may be represented as (x, y, $\lambda$). Any particular wavelength, ($\lambda$), of imaged light of the substance is associated with a set of cube images or spectral fingerprints of the substance in two dimensions, for example, along the x and y directions, whereby voxels having that value of wavelength constitute the pixels of a monochromatic image of the substance at that wavelength. Each cube image, featuring a range of wavelengths of imaged light of the substance is analyzed to produce a physical location distribution or two dimensional map of the chemical composition, or, of some other physicochemical property of the substance, for example, particle size, particle geometry, or, particle shape.

An example of a method and system for real-time, on-line chemical analysis of particulate substances, for example, polycyclic aromatic hydrocarbon (PAH) particles in aerosols, in which the PAH substance is excited to emit light for example, by fluorescence, is that of U.S. Pat. No. 5,880,830, issued to Schechter, and manufactured by Green Vision Systems Ltd. of Tel Aviv, Israel, the teachings of which are incorporated by reference for all purposes as if fully set forth herein. In the disclosed method, spectral imaging techniques are implemented to acquire an image and analyze the properties of fixed position PAH particles. As part of this method, air is sampled by means of a high volume pump sucking a large volume of air featuring aerosol contaminated with PAH particles onto a substrate, followed by on-line imaging and scene analysis of the stationary particles.

A method of calibration and real-time analysis of particles is described in U.S. Pat. No. 6,091,843, to Moshe et al., the teachings of which are incorporated by reference for all purposes as if fully set forth herein. The method described, is based on using essentially the same system of U.S. Pat. No. 5,880,830, for acquiring spectral images of static particles on a filter. In brief, there is disclosed a method of analyzing particles for the presence of chemical or biological species, by spectral imaging of the particles. The output of the image acquisition is, for each imaged portion of a two-dimensional surface host to the particles, a set of images, each image at a different wavelength. These images are digitized and analyzed by standard image processing methods to produce, for each imaged portion of the two-dimensional surface, spectral images of targets, which are then compared to calibration spectral images of standard targets, for identifying and characterizing the unknown chemical or biological targets or species associated with the particles.

In the disclosure of U.S. Pat. No. 6,091,843, targets are identified in static particle images and are classified according to morphology or structural type and spectrum type. Each target is assigned a value of an extensive property. A descriptor vector is formed, where each element of the descriptor vector is the sum of the extensive property values for one target class. The descriptor vector is transformed, for example, to a vector of mass concentrations of chemical species of interest or of number concentrations of biological species of interest, using a relationship determined in the calibration procedure. In the calibration procedure, spectral images of calibration samples of static particles having known composition are acquired, and empirical morphology types and spectrum types are inferred from the spectral images. Targets are identified in the calibration spectral images, classified according to morphology type and spectrum type, and assigned values of an extensive property. For each calibration sample, a calibration descriptor vector and a calibration concentration vector is formed. A collective relationship between the calibration descriptor vectors and the calibration concentration vectors is found using chemometric methods.

In conventional scene analysis using the above described methods and systems for spectral imaging of individual particles, for example, for each scene, there is auto-focusing, where a best focal position is determined for use in analyzing or classifying particle properties. For some scenes, this is possible, and a focused image may be obtained in an automatic manner. Typically, an auto-focus module is coupled with a computer controlled mechanism that automatically changes the focal position, by moving along an axis parallel to the optical axis of the imaging or focusing sensor, thereby enabling identification of a good focal position. For other scenes, a good focal position is not guaranteed to exist and further image processing based on focus-fusion methodology is required.

When focused images of spatially varying or depth dependent scenes can not be generated by using such auto-focus electro-mechanical means, such that single focal positions can not be identified, focused representations of the scenes can be constructed by combining or fusing selected portions of several defocused images of each scene. This process is referred to as focus-fusion imaging, and the resulting images of such processing are referred to as a focus-fusion images. Defocused images, for example, those acquired during auto-focusing, are fused together such that each target in a given scene is in correct focus. Scene targets are detected by analyzing either focused images, if they exist, or, focus-fusion images.

Spectral imaging of spatially varying, depth dependent or multi-layered samples of particles is not described in the above referenced methods and systems. Imaging and image analysis of a random single two-dimensional layer of a particulate substance are ordinarily straightforward. However, multi-layer imaging and image analysis of depth dependent particulate substances, such as multi-layered dry particles, or, particles in a frozen or immobilized suspension, for example, as obtained from a pharmaceutical, or, food or beverage, particulate sample, are substantially more complex. Nevertheless, there are instances where it is necessary to obtain property and classification information of depth dependent particulate substances, in-situ, for example, as part of sampling a commercial pharmaceutical, or, food or beverage, manufacturing process. More often than not, images obtained of such particulate substances are defocused, and require special image processing techniques, such as focus-fusion, for obtaining useful information about the particulate substances.

Additionally, the above described disclosures feature useful methods and systems for acquiring and analyzing spectral images of particles, but are limited to identifying and quantifying the presence of species on particles, where the species are typically considered particle impurities, and therefore, there is no description of spectral imaging and analysis of a chemically pure particulate substance. Furthermore, there is no description of a method for applying the described pattern recognition classification procedures for analyzing and correlating 'intra-particle' spectral images of individual particles with respect to morphological or geometrical distribution and/or frequency distribution of physicochemical properties and characteristics, such as concentration, density, particle size, particle geometry, particle shape, particle porosity, and crystallographic parameters, of the at least one chemically pure particulate substance in the host particles, separate from impurity species concentration.

There is disclosed, by the same applicant of the present invention, in PCT International Patent Application No. PCT/IL01/01110, filed Dec. 2, 2001, entitled: "Method For In-situ Focus-fusion Multi-layer Spectral Imaging And Analysis Of Particulate Samples", taking priority from recently allowed U.S. patent application Ser. No. 09/727,753, filed Dec. 4, 2000, of same title, which is a Continuation-in-Part of abandoned U.S. patent application Ser. No. 09/322,975, filed Jun. 1, 1999, of same title, which is a Continuation-in-Part of U.S. patent application Ser. No. 09/146,361 (now U.S. Pat. No. 6,091,843, previously summarized above), the teachings of which are incorporated by reference for all purposes as if fully set forth herein, a method for in-situ focus-fusion multi-layer spectral imaging and analysis of depth dependent particulate substances, which is applicable to crystalline particulate substances.

Therein, is described how three-dimensional scene analysis is performed by applying focus-fusion methodology to defocused images acquired by multi-layer spectral imaging of depth dependent particulate substances, whereby the results are shown to be quite useful for detecting and classifying in-situ physicochemical properties and characteristics, such as chemical composition, concentration, density, particle size, particle geometry, and particle shape, which ideally involve multi-layer three-dimensional image analysis.

According to the disclosure of PCT/IL01/01110, a unique method of focus-fusion is applied to focused and defocused images acquired from multi-layer spectral imaging of a depth dependent particulate substance, in order to construct a series of fused focused cube (spectral) image representations of the imaged particles, thereby generating a focused image of essentially each particle in a sample of the particulate substance. The disclosed method introduces and features the use of a uniquely defined and evaluated focus-fusion factor parameter, $F_b$, for correlating and integrating (1) empirically determined particle physicochemical information and parameters relating to (i) particle chemical composition and associated chemistry, and relating to (ii) particle morphology such as particle size and particle shape, with (2) empirically determined particle spectral information and parameters such as (i) pixel intensity, (ii) signal-to-noise ratio (S/N), (iii) image sharpness, (iv) spectral distances, and (v) spectral fingerprints associated with distinct spectral emission patterns of individual particles. The focus-fusion factor parameter, $F_b$, is used in critical steps of image detection, image analysis, and in algorithms for classification of particle properties and characteristics. This uniquely determined parameter enables achievement of high levels of accuracy and precision in detection and classification of the particulate substance, on a global scale, and of the individual particles, on a local scale.

The method disclosed in PCT/IL01/01110 includes collecting and analyzing physicochemical and multi-layer spectral data relating to the particles in the sample, including mapping of three-dimensional positions of particles, particle sizes, and of particle characteristics relating to particle emission spectra. Scene information, in the form of spectral fingerprints, used in the analysis of focus-fusion of the multi-layer spectral images is further processed in order to generate relevant in-situ physicochemical information of the particles, such as particle size distribution, particle morphological features such as structure, form, and shape characteristics, and chemical composition. The focus-fusion multi-layer spectral image analysis includes a sophisticated classification procedure for on-line (real time) extracting useful information relating to particle properties and characteristics needed for generating a statistically based and reliable report applicable to monitoring and/or controlling a wide variety of industrial processes, such as pharmaceutical, food, and beverage, manufacturing processes.

According to that disclosure, the method of focus-fusion multi-layer spectral imaging and analysis of depth dependent particulate samples can be applied to a sample of chemically pure particles, such as chemically pure crystalline particles. However, each described alternative procedure for analyzing the data of the fused cube images of the particles is with respect to either an individual particle as a whole, as the simplest unit or object of imaging and analysis, or, with respect to a sample of many such individual particles. There is no explicit, implicit, or even suggestive, description for analyzing the data, in general, of the fused cube images of the particles with respect to variation of internal or 'intra-particle' physicochemical properties and characteristics, and consequently, in that disclosure, there is no explicit, implicit, or suggestive, description for relating focus-fusion spectral image data, in particular, with respect to variation, in terms of morphological or geometrical distribution and/or frequency distribution, to internal or intra-particle physicochemical properties and characteristics such as concentration, density, particle size, particle geometry, particle shape, particle porosity, and/or crystallographic parameters, of the individual particles.

In actuality, it turns out, especially with regard to standard laboratory analytical testing of particulate substances as currently practiced by pharmaceutical, biotechnology, food, beverage, and chemical, industries, that from a more detailed, but realistic viewpoint, measuring, determining, and analyzing, physicochemical properties and characteristics of a sample of a particulate substance, such as of a chemically pure crystalline particulate substance, down to the level or scale of an individual particle as a whole, are significantly limited with respect to realistically, highly accurately and reproducibly, relating spectral imaging and/or other types of empirically obtained and/or determined physicochemical data and information to results of the laboratory analytical testing studies of particulate substances. This phenomenon is particularly evident where a chemically pure particulate substance, featuring at least one chemically pure individual compound, is heterogeneous with respect to variation, in terms of morphological or geometrical distribution and/or frequency distribution, of internal or intra-particle physicochemical properties and characteristics such as concentration, density, particle size, particle geometry, particle shape, particle porosity, and/or crystallographic parameters, of the at least one chemically pure individual compound throughout a given sized sample of the chemically pure particulate substance.

Accordingly, a need was clearly established for measuring, determining, and analyzing, empirically obtained and/or determined physicochemical data and information of particulate substances, with respect to variation, in terms of morphological or geometrical distribution and/or frequency distribution, of internal or intra-particle physicochemical properties and characteristics of the particulate substances, for improving analysis and understanding of the physicochemical properties, characteristics, and behavior, of the particulate substances, thereby, improving current applications and developing new applications of particulate substances for those industries, such as the biopharmaceutical, food, and beverage, industries, which process particulate substances in the form of raw materials and/or finished products.

The same applicant as the present invention, in PCT International Patent Application No. IL01/00366, filed Apr. 19, 2001, entitled "Method For Generating Intra-particle Morphological Concentration/Density Maps And Histograms Of A Chemically Pure Particulate Substance", taking priority from U.S. Provisional Patent Application No. 60/198,556, filed Apr. 20, 2000, the teachings of which are incorporated by reference for all purposes as if fully set forth herein, disclose a method for spectral imaging, in general, and focus-fusion multi-layer spectral imaging, in particular, combined with appropriate pattern recognition classification analysis, performed on a number of individual particles of a plurality of particles of a chemically pure particulate substance, for forming a plurality of sets of single-particle spectral fingerprint data, where each set is characterized by a single-particle spectral fingerprint spectrum.

According to the method disclosed in PCT/IL01/00366, in each set of single-particle spectral fingerprint data, shifts in spectral parameters, also referred to as 'spectral shifts', are identified, for forming an intra-particle region group featuring a plurality of sub-sets of intra-particle spectral fingerprint pattern data. Each sub-set is characterized by an intra-particle spectral fingerprint pattern spectrum, which is associated with the same single-particle spectral fingerprint spectrum as the other intra-particle spectral fingerprint pattern spectra of the other sub-sets in the same intra-particle region group. Each intra-particle region group is associated with a plurality of intra-particle morphological region type identifiers, where each intra-particle morphological region type identifier is associated with a surface concentration value and a density value of the chemically pure substance in that imaged particle, for forming a set of intra-particle morphological concentration/density data. For each particle, the set of intra-particle morphological concentration/density data is used for generating an intra-particle morphological concentration/density map for illustrating local, intra-particle, morphological distribution of surface concentration and density of the chemically pure substance throughout the imaged particle. For that number of imaged and analyzed particles of the plurality of particles of the particulate substance, a morphological concentration/density histogram, or frequency distribution, is generated from a plurality of sets of the intra-particle morphological concentration/density data, for illustrating a statistically based global morphological distribution of concentration and density throughout the entire chemically pure particulate substance.

The method disclosed in PCT/IL01/00366, introducing and featuring the newly determined sub-classification of spectral imaging data, in general, and of focus-fusion multi-layer spectral imaging data, in particular, illustrates how it is possible, by way of identifying, analyzing, and correlating spectral shifts, to associate different spectral fingerprint patterns of the same particle with different intra-particle morphological regions varying in concentration and/or density of the chemically pure, but morphologically heterogeneous, particulate substance. The novelty of that method is based on identifying shifts in spectral parameters, for example, emission wavelength and/or emission intensity or amplitude, present in classified spectral imaging spectral fingerprint data, in general, and based on identifying shifts in spectral parameters in classified focus-fusion multi-layer spectral imaging spectral fingerprint data, in particular, and using the identified spectral shift data for revealing, correlating, and displaying intra-particle morphological and concentration/density data in the forms of intra-particle morphological concentration/density maps and histograms of the chemically pure particulate substance, which are representative of, and directly applicable to, intra-particle physicochemical analysis and characterization of a chemically pure particulate substance.

The method of that invention, compared to currently used methods, provides new capabilities for effectively and efficiently determining and classifying intra-particle morphological concentration/density data and related information, for application to a wide variety of industries requiring intra-particle physicochemical analysis and characterization of chemically pure particulate substances, such as chemically pure crystalline particulate substances. That invention is especially well suited for analyzing spectral images of chemically pure particulate substances of medicines, for example, medicines containing both chemically pure active ingredients and chemically pure inactive ingredients, whereby there is distinguishing and characterizing physicochemical properties, characteristics, and behavior, of both active and inactive ingredients.

As previously stated above, in the field of commercial handling, processing, and manufacturing, of crystalline particulate substances, including analysis and control thereof, especially as applied in the biopharmaceutical industry, there is on-going interest, resources, and activities, being devoted to techniques for measuring, determining, and analyzing, physicochemical data and information relating to crystallographic properties, characteristics, and parameters, of crystalline particulate substances, in general, and of chemically pure crystalline particulate substances, in particular. The above is especially relevant when involving chemically pure crystalline particulate substances each featuring or characterized by more than one unique set of crystallographic parameters of crystal type and crystal class.

More specifically, for example, in a chemically pure crystalline particulate substance, one or more of the at least one chemically pure individual chemical compound may exhibit isomerism, involving the existence of a variety of structural isomers and/or stereoisomers of the same chemically pure crystalline particulate substance, typically, characterized by a corresponding variety of different crystallographic parameters of crystal type and crystal class. To a lesser, but, nevertheless, still noticeable, extent or degree of structural or crystallographic difference, one or more of the at least one chemically pure individual chemical compound may exhibit polymorphism, involving crystallization of a compound in at least two distinct forms, giving rise to the existence of a variety of structurally different polymorphs of the same chemically pure crystalline particulate substance, typically, characterized by a corresponding variety of different crystallographic parameters of crystal type and crystal class.

Moreover, in such cases, according to extent of separation and purification processes included in the overall manufacturing processes involving the chemically pure crystalline particulate substance, the chemically pure crystalline particulate substance is expected to be heterogeneous to some degree or extent with respect to morphological or geometrical distribution and/or with respect to frequency distribution of crystallographic parameters of crystal type and crystal class, of the at least one chemically pure individual compound throughout a given sized sample of the chemically pure crystalline particulate substance.

It is well known and very relevant to the biopharmaceutical industry, that different isomers and/or polymorphs of the same chemically pure crystalline particulate substance may exhibit significantly different physicochemical properties and characteristics, such as those related to crystallographic parameters, giving rise to significantly different behavior, efficacy, and therapeutic effects, when subjected to the same laboratory in-vitro conditions and/or clinical in-vivo conditions.

An excellent, realistic example of current concern, of this phenomenon relates to a patented brand name drug, and an almost identical generic substitute drug, each marketed to and consumed by post-menopausal women exhibiting symptoms of osteoporosis. Both drugs contain the identically same active ingredient, alendronic acid. However, while the patented brand name drug is manufactured, sold, and consumed, as a sodium trihydrate, having 'three' water molecules in the crystalline particulate structure, the almost identical generic substitute drug is manufactured, sold, and consumed, as a sodium monohydrate, having a 'single' water molecule in the crystalline particulate structure. In time, a clinically statistically significant number of women consuming the sodium monohydrate generic substitute drug developed and exhibited a wide variety of undesirable and/or severe physiological symptoms and medical conditions, apparently directly related to their consumption of the sodium monohydrate generic substitute drug, which were not reported by similar women consuming the sodium trihydrate brand name drug.

From the example just described, it is clearly expected, and may be concluded a priori, that intra-particle crystallographic parameters of crystal type and crystal class of particles of the sodium monohydrate drug are measurably different from those of particles of the sodium monohydrate drug, to the extent that the previously described phenomenon takes place. In this case, crystallographic parameters can therefore be used as criteria of quality control and/or quality assurance testing during the manufacturing of the drug. This represents just one example of the need for the present invention, of a method for generating intra-particle crystallographic parameter maps and histograms of a chemically pure crystalline particulate substance, by spectral imaging of individual particles of the chemically pure crystalline particulate substance and analyzing the spectral images using pattern recognition classification analysis, which is not fulfilled by implementing prior art techniques and methodologies of spectral imaging of particles.

In the disclosure of PCT/IL01/00366 it is stated "that spectral shifts present in a given group of intra-particle spectral fingerprint patterns of an individual particle are primarily due to local, intra-particle, variation or heterogeneity in particle morphology such as shape or geometry, and porosity, and due to local, intra-particle, variation or heterogeneity in surface concentration and/or density of the chemically pure substance". An important aspect of particle morphology regarding particle shape or geometry, not mentioned or described in, and not obviously derived from, the prior art of spectral imaging, in general, or from the disclosure of PCT/IL01/00366, in particular, is that of crystallographic parameter characterization of crystalline particles, and of crystalline particulate substances consisting of and/or including crystalline particles in their compositions. To date, the inventor of the present invention is unaware of a prior art teaching of a method for generating intra-particle crystallographic parameter maps and histograms of a chemically pure crystalline particulate substance by spectral imaging of individual particles of the chemically pure crystalline particulate substance and analyzing the spectral images using pattern recognition classification analysis.

There is thus a need for, and it would be highly advantageous to have a method for generating intra-particle crystallographic parameter maps and histograms of a chemically pure crystalline particulate substance by spectral imaging, in general, and by focus-fusion multi-layer spectral imaging, in particular, of individual particles of the chemically pure crystalline particulate substance and analyzing the spectral images using pattern recognition classification analysis. Moreover, there is a need for such a method which is applicable to a variety of industries, such as the biopharmaceutical, food, and beverage, industries, currently devoting significant amounts of resources towards better measurement analysis, understanding, and application, of crystallographic data, information, and parameters, of chemically pure crystalline particulate substances in the form of raw materials and/or finished products. Additionally, there is a particular need especially relevant to those sectors of the biopharmaceutical industry currently or considering developing, testing, and manufacturing, pharmaceutical products which include chemically pure crystalline particulate substances featuring different isomers and/or polymorphs exhibiting significantly different physicochemical properties and characteristics that are a function of crystallographic parameters, giving rise to significantly different behavior, efficacy, and therapeutic effects, when subjected to the same laboratory in-vitro conditions and/or clinical in-vivo conditions.

SUMMARY OF THE INVENTION

The present invention relates to a method for generating intra-particle crystallographic parameter maps and histograms of a chemically pure crystalline particulate substance by spectral imaging, in general, and by focus-fusion multi-layer spectral imaging, in particular, of individual particles of the chemically pure crystalline particulate substance and analyzing the spectral images using pattern recognition classification analysis.

Thus, according to the present invention, there is provided a method for generating intra-particle crystallographic parameter maps and histograms of a chemically pure crystalline particulate substance, comprising the steps of. (a) acquiring a set of spectral images by a spectral imaging system for each of a number of particles of the chemically pure crystalline particulate substance having a plurality of the particles; (b) performing pattern recognition classification analysis on each set of the acquired spectral images for each imaged particle, for forming a number of sets of single-particle spectral fingerprint data; (c) identifying at least one spectral shift in each set of single-particle spectral fingerprint data associated with each imaged particle, for forming an intra-particle crystallographic region group featuring a plurality of sub-sets of intra-particle spectral fingerprint pattern data, where selected data elements in each sub-set are shifted relative to corresponding data elements in each remaining sub-set in the same intra-particle crystallographic region group; (d) forming a set of intra-particle crystallographic parameter data relating to each imaged particle from each intra-particle crystallographic region group; (e) generating each of the intra-particle crystallographic parameter maps from each set of the intra-particle crystallographic parameter data; and (f) generating each of the crystallographic parameter histograms from a plurality of the sets of the intra-particle crystallographic parameter data, for illustrating a statistically based global morphological or geometrical frequency distribution of crystallographic parameters of the chemically pure particulate crystalline substance throughout the chemically pure crystalline particulate substance.

According to further features in preferred embodiments of the invention described below, the chemically pure crystalline particulate substance is a crystalline particulate substance including a plurality of crystalline particles each having at least one chemically pure individual chemical compound.

According to further features in preferred embodiments of the invention described below, the at least one chemically pure individual chemical compound exhibits isomerism and/or polymorphism, and has a number of isomers and/or a number of polymorphs.

According to further features in preferred embodiments of the invention described below, the chemically pure crystalline particulate substance is heterogeneous with respect to morphological or geometrical distribution of crystallographic parameters of crystal type and crystal class, of at least one chemically pure individual compound throughout a sample of the chemically pure crystalline particulate substance.

According to further features in preferred embodiments of the invention described below, the physicochemical properties and characteristics of the chemically pure crystalline particulate substance are selected from the group consisting of independent of particle depth and dependent of particle depth.

According to further features in preferred embodiments of the invention described below, the chemically pure crystalline particulate substance is selected from the group consisting of a separate stand alone powdered entity or substance, and a powdered entity or substance part of another entity or substance in a solid or liquid phase having a function selected from the group consisting of as a substrate of, containing, hosting, delivering, receiving, and combinations thereof, the chemically pure crystalline particulate substance.

According to further features in preferred embodiments of the invention described below, the chemically pure crystalline particulate substance is a powder in a form selected from the group consisting of a powder and a powder mixture. The powder is in a configuration or form selected from the group consisting of loose or free flowing, packed, compacted, and combinations thereof The powder is composed of components selected from the group consisting of inorganic components, organic components, and combinations thereof The powder is of origin or derivation selected from the group consisting of natural origin or derivation, synthetic origin or derivation, and combinations thereof According to further features in preferred embodiments of the invention described below, the chemically pure crystalline particulate substance is a raw material used in manufacturing a product selected from the group consisting of a pharmaceutical product, a food product, and a beverage product.

According to further features in preferred embodiments of the invention described below, the chemically pure crystalline particulate substance is selected from the group consisting of a medicinal or therapeutic powder, a high performance powdered chemical, and a powdered biological specimen. The medicinal or therapeutic powder is part of a pharmaceutical product in a form selected from the group consisting of a tablet a capsule, a caplet, a loose powder, a gel, a liquid suspension, and a liquid solution.

According to further features in preferred embodiments of the invention described below, in step (a), the spectral images are focus-fusion multi-layer spectral images acquired by focus-fusion multi-layer spectral imaging of the particles of the chemically pure crystalline particulate substance.

According to another aspect of the present invention, there is provided a method for identifying and illustrating intra-particle morphological or geometrical distribution of crystallographic parameters of a chemically pure crystalline particulate substance, comprising the steps of: (a) acquiring a set of spectral images by a spectral imaging system for each of a number of particles of the chemically pure crystalline particulate substance having a plurality of the particles; (b) performing pattern recognition classification analysis on each set of the acquired spectral images for each imaged particle, for forming a number of sets of single-particle spectral fingerprint data; (c) identifying at least one spectral shift in each set of single-particle spectral fingerprint data associated with each imaged particle, for forming an intra-particle crystallographic region group featuring a plurality of sub-sets of intra-particle spectral fingerprint pattern data, where selected data elements in each sub-set are shifted relative to corresponding data elements in each remaining sub-set in same intra-particle crystallographic region group; (d) forming a set of intra-particle crystallographic parameter data relating to each imaged particle from each intra-particle crystallographic region group; and (e) generating a plurality of intra-particle crystallographic parameter maps and histograms from a plurality of the sets of the intra-particle crystallographic parameter data, for identifying and illustrating the intra-particle morphological or geometrical distribution of the crystallographic parameters of the chemically pure particulate crystalline substance throughout the chemically pure crystalline particulate substance.

The present invention successfully provides a new, highly accurate and reproducible, method for generating and applying intra-particle crystallographic parameter data and information of a chemically pure crystalline particulate substance by spectral imaging, in general, and by focus-fusion multi-layer spectral imaging, in particular, combined with analyzing the spectral images using pattern recognition classification analysis, and widens the scope of presently known techniques and methods for spectral imaging of particulate substances. Additionally, the method of the present invention is applicable to a variety of industries, such as the biopharmaceutical, food, and beverage, industries, currently devoting significant amounts of resources towards better measurement analysis, understanding, and application, of crystallographic data, information, and parameters, of chemically pure crystalline particulate substances in the form of raw materials and/or finished products.

Implementation of the method of the present invention involves performing or completing selected tasks or steps manually, automatically, or a combination thereof. Moreover, according to actual instrumentation and/or equipment used for implementing a particular preferred embodiment of the disclosed method, several selected steps of the present invention could be performed by hardware, by software on any operating system of any firmware, or a combination thereof. In particular, as hardware, selected steps of the invention could be performed by a computerized network, a computer, a computer chip, an electronic circuit, hard-wired circuitry, or a combination thereof, involving any number of digital and/or analog, electrical and/or electronic, components, operations, and protocols. Additionally, or alternatively, as software, selected steps of the invention could be performed by a data processor, such as a computing platform, executing a plurality of computer program types of software instructions or protocols using any suitable computer operating system.

BRIEF DESCRIPTION OF THE DRAWINGS

The present invention is herein described, by way of example only, with reference to the accompanying drawings. With specific reference now to the drawings in detail, it is stressed that the particulars shown are by way of example and for purposes of illustrative description of the preferred embodiments of the present invention only, and are presented in the cause of providing what is believed to be the most useful and readily understood description of the principles and conceptual aspects of the present invention. In this regard, no attempt is made to show structural details of the present invention in more detail than is necessary for a fundamental understanding of the invention, the description taken with the drawings making apparent to those skilled in the art how the several forms of the invention may be embodied in practice. In the drawings.

DESCRIPTION OF THE PREFERRED EMBODIMENTS

The present invention relates to a method for generating intra-particle crystallographic parameter maps and histograms of a chemically pure crystalline particulate substance by spectral imaging, in general, and by focus-fusion multi-layer spectral imaging, in particular, of individual particles of the chemically pure crystalline particulate substance and analyzing the spectral images using pattern recognition classification analysis.

While searching for a method of applying spectral imaging, in general, and focus-fusion multi-layer spectral imaging (focusing on a single particle layer or a multiple of particle layers, where each layer corresponds to one spectral image cube per field-of-view of a spectral imaging device), in particular, combined with pattern recognition classification analysis for improving physicochemical characterization of a sample of a chemically pure, but morphologically heterogeneous, particulate substance, it was unexpectedly determined at the single particle level, that each spectrum, in each group of spectra associated with a set of imaged targets, or 'Blobs' (the terms 'targets' and 'Blobs' are clearly defined and described in detail in previously cited PCT International Patent Application No. PCT/IL01/01110, summarized hereinabove in the Background section), within the same particle and assigned the same spectral fingerprint of that particle, features spectral parameters, for example, emission wavelength and/or emission intensity or amplitude, shifted with respect to the corresponding same spectral parameters of each of the remaining spectra of that same group of spectra. Accordingly, each spectrum in each such group of spectra corresponds to a different particular pattern of the same spectral fingerprint assigned to that group of spectra, associated with an imaged particle. Herein, a pattern of a spectral fingerprint associated with a set of spectra is referred to as a 'spectral fingerprint pattern'. Thus, each group of spectra associated with a characteristic spectral fingerprint of the particle features a plurality of intra-particle spectral fingerprint patterns of the imaged particle.

As previously cited and summarized in the Background section, above, in PCT Patent Application No. IL01/00366, the same applicant as the present invention disclosed a "Method For Generating Intra-particle Morphological Concentration/Density Maps And Histograms Of A Chemically Pure Particulate Substance", taking priority from U.S. Provisional Patent Application No. 60/198,556, filed Apr. 20, 2000, the teachings of which are incorporated by reference for all purposes as if fully set forth herein. In that disclosure, the newly determined sub-classification of the spectral imaging data, in general, and of the focus-fusion multi-layer spectral imaging data, in particular, provides an accurate and precise way of identifying, analyzing, and correlating spectral shifts, to associate different spectral fingerprint patterns of the same particle with different intra-particle morphological regions varying in concentration and/or density of the chemically pure, but morphologically heterogeneous, particulate substance.

Also, as previously stated, in the field of commercial handling, processing, and manufacturing, of crystalline particulate substances, including analysis and control thereof, especially as applied in the biopharmaceutical industry, there is on-going interest, resources, and activities, being devoted to techniques for measuring, determining, and analyzing, physicochemical data and information relating to crystallographic properties, characteristics, and parameters, of crystalline particulate substances, in general, and of chemically pure crystalline particulate substances, in particular. The above is especially relevant when involving chemically pure crystalline particulate substances each featuring or characterized by more than one unique set of crystallographic parameters of crystal type and crystal class.

More specifically, for example, in a chemically pure crystalline particulate substance, one or more of the at least one chemically pure individual chemical compound may exhibit isomerism, involving the existence of a variety of structural isomers and/or stereoisomers of the same chemically pure crystalline particulate substance, typically, characterized by a corresponding variety of different crystallographic parameters of crystal type and crystal class. To a lesser, but, nevertheless, still noticeable, extent or degree of structural or crystallographic difference, one or more of the at least one chemically pure individual chemical compound may exhibit polymorphism, involving crystallization of a compound in at least two distinct forms, giving rise to the existence of a variety of structurally different polymorphs of the same chemically pure crystalline particulate substance, typically, characterized by a corresponding variety of different crystallographic parameters of crystal type and crystal class.

Moreover, in such cases, according to extent of separation and purification processes included in the overall manufacturing processes involving the chemically pure crystalline particulate substance, the chemically pure crystalline particulate substance is expected to be heterogeneous to some degree or extent with respect to morphological or geometrical distribution and/or with respect to frequency distribution of crystallographic parameters of crystal type and crystal class, of the at least one chemically pure individual compound throughout a given sized sample of the chemically pure crystalline particulate substance.

In the disclosure of PCT/IL01/00366 it is stated "that spectral shifts present in a given group of intra-particle spectral fingerprint patterns of an individual particle are primarily due to local, intra-particle, variation or heterogeneity in particle morphology such as shape or geometry, and porosity, and due to local, intra-particle, variation or heterogeneity in surface concentration and/or density of the chemically pure substance". An important aspect of particle morphology regarding particle shape or geometry, not mentioned or described in, and not obviously derived from, the prior art of spectral imaging, in general, or from the disclosure of PCT/IL01/00366, in particular, is that of crystallographic parameter characterization of crystalline particles, and of crystalline particulate substances consisting of and/or including crystalline particles in their compositions. The method for generating intra-particle crystallographic parameter maps and histograms of a chemically pure crystalline particulate substance, of the present invention, is herein disclosed for the first time, and is neither anticipated or obviously derived from the methods disclosed in PCT/IL01/01110 or in PCT/IL01/00366, either singly or in combination.

In a crystalline solid, herein, referred to as a crystalline particulate substance, to be distinguished from noncrystalline substances such as liquids and amorphous solids or amorphous particulate substances, structurally, the constituent particles, compounds, atoms, molecules, or ions, are arranged in an orderly, repetitive pattern or crystal structure in three dimensions. Herein, the term 'chemically pure crystalline particulate substance' refers to a crystalline particulate substance featuring a plurality of crystalline particles each composed of at least one chemically pure individual chemical compound, where the chemically pure crystalline particulate substance is typically heterogeneous with respect to morphological or geometrical distribution and/or with respect to frequency distribution of physicochemical properties and characteristics, such as concentration, density, particle size, particle geometry, particle shape, particle porosity, and crystallographic parameters of crystal type and crystal class, of the at least one chemically pure individual compound throughout a given sized sample of the chemically pure crystalline particulate substance. Moreover, any number of these physicochemical properties and characteristics of the crystalline particulate substance are either independent of particle depth, or are dependent upon particle depth.

The present invention focuses on aspects relating to the morphological or geometrical distribution and frequency distribution of crystallographic parameters of at least one chemically pure individual compound throughout a given sized sample of a chemically pure crystalline particulate substance comprised of the at least one chemically pure individual compound. An exemplary particular application of the present invention is in those sectors of the biopharmaceutical industry currently or considering developing, testing, and manufacturing, pharmaceutical products which include chemically pure crystalline particulate substances featuring compounds having different isomers and/or polymorphs exhibiting significantly different physicochemical properties and characteristics that are a function of crystallographic parameters, giving rise to significantly different behavior and therapeutic effects, when subjected to the same laboratory in-vitro conditions and/or clinical in-vivo conditions.

The present invention is applicable to a chemically pure crystalline particulate substance which is a powder or powder mixture in a configuration or form selected from the group consisting of loose or free flowing, packed, compacted, and combinations thereof, being composed of inorganic and/or organic components, and being of natural and/or synthetic origin or derivation. Moreover, the chemically pure crystalline particulate substance is either a separate stand alone powdered entity or substance, or part of another entity or substance in a solid or liquid phase functioning or behaving as a substrate, containing, hosting, delivering, and/or receiving, the chemically pure crystalline particulate substance.

Exemplary types of chemically pure crystalline particulate substances specifically used in the biopharmaceutical industry are naturally and/or synthetically derived medicinal or therapeutic powders or powder mixtures, high performance powdered chemicals, and powdered biological specimens, each featuring at least one active ingredient and/or at least one inactive ingredient, as part of a raw material and/or an eventual finished pharmaceutical product formulated as a tablet, capsule, caplet, loose powder, gel, liquid suspension, or, liquid solution. Exemplary types of chemically pure crystalline particulate substances specifically used in the food and beverage industries are naturally and/or synthetically derived powders or powder mixtures, and high performance powdered chemicals, functioning as flavor, preservative, and/or, consistency enhancers, featuring at least one chemically pure crystalline particulate substance either in the raw material(s) and/or in the eventual finished food or beverage product formulated as a loose or free flowing, packed, compacted, stand alone powdered substance, or, as part of another food or beverage substance.

It is well known to one of ordinary skill in the art that there are four main types of crystals, according to the types of bonds and interactive forces operative in binding the individual species into a particular crystal. These are (i) metallic crystals, (ii) ionic crystals, (iii) van der Waals crystals, and (iv) covalent crystals. Furthermore, crystalline particulate substances are ordinarily classified into seven crystal systems, that is, triclinic, monoclinic, orthorhombic, hexagonal, tetragonal, rhombohedral, and cubic, according to the shape and geometrical dimensions (lengths and directions or angles of inclinations of the vectors) of the unit cell of the crystalline particulate substance. Moreover, a further division for characterizing crystalline particulate substances is made into thirty-two crystal classes, according to the combinations of symmetry elements which are compatible with each crystal system, where an element of symmetry is an operation which brings the crystal into coincidence with itself, such as rotation about an axis, reflection in a plane, inversion through a center of symmetry, and rotation inversion. It is also well known in the art and science of crystallography that there is a total of two-hundred and thirty-two possible combinations, referred to as space groups, of the symmetry elements of the thirty-two different crystal classes, whereby, any atomic arrangement in a crystal must have the symmetry corresponding to one of these space groups of symmetry operations. Ordinarily, to identify or determine the space group of a crystalline particulate substance requires a detailed examination of the crystal by x-rays.

The scope, novelty, and inventiveness, of the present invention are based on identifying shifts in spectral parameters, for example, emission wavelength and/or emission intensity or amplitude, present in classified spectral imaging spectral fingerprint data, in general, and based on identifying shifts in spectral parameters in classified focus-fusion multi-layer spectral imaging spectral fingerprint data, in particular, and using the identified spectral shift data for revealing, correlating, and displaying intra-particle crystallographic parameter data in the forms of intra-particle crystallographic parameter maps and histograms of the chemically pure crystalline particulate substance, which are representative of, and directly applicable to, intra-particle physicochemical analysis and characterization of the chemically pure crystalline particulate substance.

It is to be understood that the present invention is not limited in its application to the details of the order or sequence of steps of operation or implementation of the method, or, to the details of construction, arrangement, and composition of the components of the device, set forth in the following description, drawings, or examples. The present invention is capable of other embodiments or of being practiced or carried out in various ways. Although methods and materials similar or equivalent to those described herein can be used for practicing or testing the present invention, suitable methods and materials are described herein.

It is also to be understood that unless otherwise defined, all technical and scientific words, terms, and/or phrases, used herein have the same meaning as commonly understood by one of ordinary skill in the art to which this invention belongs. Phraseology, terminology, and notation, employed herein are for the purpose of description and should not be regarded as limiting.

Steps, components, operation, and implementation of the method for generating intra-particle crystallographic parameter maps and histograms of a chemically pure crystalline particulate substance by spectral imaging, in general, and by focus-fusion multi-layer spectral imaging, in particular, of individual particles of the chemically pure crystalline particulate substance and analyzing the spectral images using pattern recognition classification analysis, according to the present invention, are better understood with reference to the following description and the accompanying drawings. Throughout the following description and accompanying drawings, like reference numbers refer to like elements.

In Step (a) of the method for generating intra-particle crystallographic parameter maps and histograms of a chemically pure crystalline particulate substance, there is acquiring a set of spectral images, in general, and acquiring a set of focus-fusion multi-layer spectral images of one or more particle layers, in particular, by using a spectral imaging system and method thereof, for each of a number of particles of the chemically pure crystalline particulate substance having a plurality of particles.

In Step (b), there is performing pattern recognition classification analysis on the set of the acquired spectral images, in general, and on the set of the acquired focus-fusion multi-layer spectral images, in particular, for each of the number of imaged particles of the chemically pure crystalline particulate substance, for forming at least the same number of sets of single-particle spectral fingerprint data, where each set of single-particle spectral fingerprint data is associated with a single particle. The plurality of sets of the single-particle spectral fingerprint data is stored in a single-particle scenario database.

Steps (a) and (b) are performed according to the previously summarized same applicant disclosures of PCT Patent Application No. PCT/IL01/01110, U.S. Pat. No. 6,091,843, and U.S. Pat. No. 5,880,830, the teachings of each of which are incorporated by reference for all purposes as if fully set forth herein. For understanding and implementing the present invention, particularly with respect to Steps (a) and (b), the following description, based on and integrating methodologies of the above cited disclosures, along with reference to FIG. 1 of the present disclosure, is herein provided.

Figure 1:
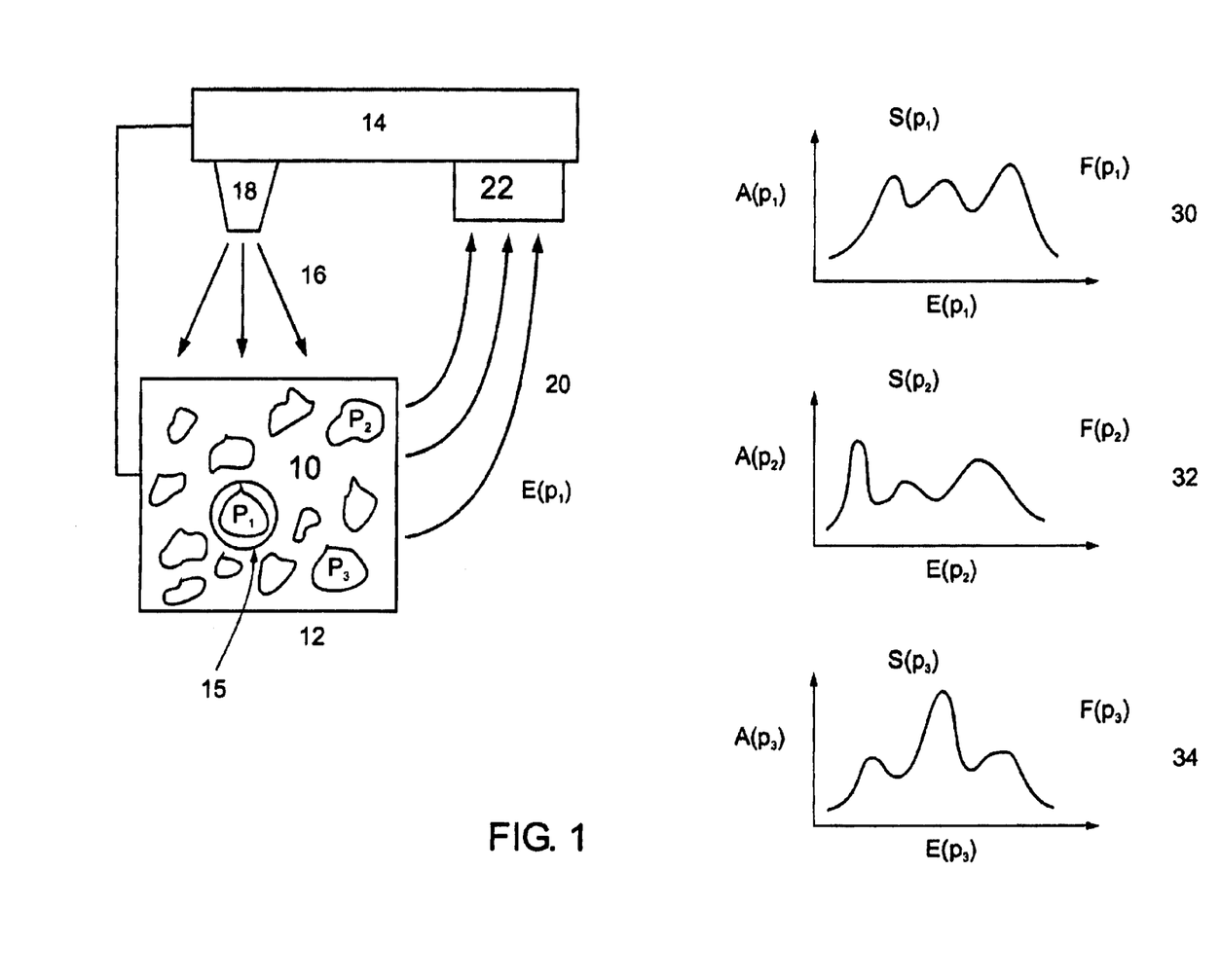
FIG. 1 is an illustration of spectral imaging, in general, and focus-fusion multi-layer spectral imaging, in particular, of a chemically pure crystalline particulate substance featuring intra-particle heterogeneous morphology and regions of varying crystallographic parameters of crystal type and crystal class, in accordance with the present invention.

Referring now to FIG. 1, an illustration of spectral imaging, in general, and focus fusion multi layer spectral imaging, in particular, of a chemically pure crystalline particulate substance featuring intra-particle heterogeneous morphology and regions of varying crystallographic parameters, chemically pure crystalline particulate substance 10, featuring a plurality of N individual particles, is positioned in an imaging sample holding device 12 such as a three-dimensional xyz translation stage, part of spectral imaging system 14, where spectral imaging system 14 is operative for detecting, acquiring, measuring, processing, and displaying spectral imaging data and information, in general, and focus-fusion multi-layer spectral imaging data and information, in particular. Imaging source energy 16, preferably, but not limited to, electromagnetic radiation, supplied by imaging energy source 18, is incident upon substance 10, and is affected by any combination of absorption, reflection, transmission, diffraction, and/or scattering, mechanisms, by each imaged particle, $p_i$, for a number, n, of imaged particles, for i–1 to n, where n is less than or equal to N. Spectral imaging system 14 collects affected energy 20 by energy collector 22.

Specifically, in accordance with the method for in-situ focus-fusion multi-layer spectral imaging and analysis of particulate samples as disclosed in PCT Patent Application No. PCT/IL01/01110, in Step (a), there is scanning chemically pure crystalline particulate substance 10, by adjusting and setting spectral imaging system 14 for spectral imaging at a selected field of view, $FOV_i$, for example, field of view 15, over crystalline particulate substance 10, having central (x, y) coordinates relative to translation stage 12, by moving translation stage 12 increments of $\Delta x$ and $\Delta y$. Then, there is acquiring a cube (spectral) plane image of crystalline particulate substance 10, in the selected i-th field of view, $FOV_i$, at a selected j-th differential imaging or focusing distance, $\Delta z_{ij}$, by focusing imaging system 14 by moving translation stage 12 in the z-direction an increment $\Delta z$, until receiving a sharp gray level image of crystalline particulate substance 10. This corresponds to adjusting and setting imaging system 14 for spectral imaging crystalline particulate substance 10 in the x-y plane of the i-th field of view, $FOV_i$, for a selected imaging distance defined along the z-axis between crystalline particulate substance 10 and the light illumination source 18 of imaging system 14. This step of acquiring spectral data and information is used for constructing a single 'focused' cube (spectral) plane image of crystalline particulate substance 10, in accordance with the method described in PCT/IL01/01110.

In addition to applying the method disclosed in PCT/IL01/01110, and not described or suggested in that disclosure, in Step (a) of the present invention, there is further sub-incrementally scanning chemically pure crystalline particulate substance 10, by 'finely' adjusting and setting spectral imaging system 14 for obtaining a plurality of spectral images by spectral imaging within a same selected field of view, $FOV_i$, for example, within same field of view 15, over crystalline particulate substance 10, having central (x, y) coordinates relative to translation stage 12, by finely moving translation stage 12 sub-increments of $\Delta x'$ and $\Delta y'$. Then, there is acquiring a corresponding plurality of cube (spectral) plane images of crystalline particulate substance 10, within the same selected i-th field of view, $FOV_i$, at the selected j-th differential imaging or focusing distance, $\Delta z_{ij}$, by focusing imaging system 14 by moving translation stage 12 in the z-direction an increment $\Delta z$, until receiving a sharp gray level image of crystalline particulate substance 10. This corresponds to adjusting and setting imaging system 14 for spectral imaging crystalline particulate substance 10 at a plurality of x, y positions or coordinates in the x-y plane of the same i-th field of view, $FOV_i$, for a selected imaging distance defined along the z-axis between crystalline particulate substance 10 and the light illumination source 18 of imaging system 14. This step of acquiring spectral data and information is used for constructing a plurality of single 'focused' cube (spectral) plane images of crystalline particulate substance 10, in accordance with the method described in PCT/IL01/01110.

Further sub-incrementally scanning chemically pure crystalline particulate substance 10 by finely moving translation stage 12 sub-increments of $\Delta x'$ and $\Delta y'$, is novel and beneficial with respect to enhancing and improving spatial acquisition and spatial pattern recognition and classification analysis of the focus-fusion multi-layer and multi-intra field of view spectral imaging data and information relating to crystallographic parameters of chemically pure crystalline particulate substance 10.

In accordance with the spectral imaging method described in PCT/IL01/01110, in substance 10, for each imaged particle, $p_i$, for example, $p_1$, $p_2$, and $p_3$, a set of spectral images, in general, and a set of focus-fusion multi-layer spectral images, in particular, is acquired. Pattern recognition classification analysis is performed on each set of the acquired spectral images, in general, and on each set of the focus-fusion multi-layer spectral images, in particular, for each imaged particle, pi, of a number of imaged particles, for example, $p_1$, $p_2$, and $p_3$, for forming an equal number of sets of single-particle spectral fingerprint data, $F(p_i)$, for example, $F(p_1)$, $F(p_2)$, and $F(p_3)$, respectively, where each set of single-particle spectral fingerprint data is associated with a single imaged particle, as shown in FIG. 1.

Each set of single-particle spectral fingerprint data, $F(p_i)$, is characterized by a single-particle spectral fingerprint spectrum, $S(p_i)$, featuring intensity or amplitude, $A(p_i)$, plotted as a function of affected energy, $E(p_i)$, 20 collected during imaging particle, $p_i$, by spectral imaging system 14. Preferably, affected energy, $E(p_i)$, 20 is expressed in terms of wavelength, frequency, or wavenumber, of electromagnetic radiation, such as fluorescent or phosphorescent light, emitted by an imaged particle, $p_i$. This data is stored in a single-particle scenario database. This process is clearly illustrated in FIG. 1, where each set of single-particle spectral fingerprint data, $F(p_1)$, $F(p_2)$, and $F(p_3)$, for each imaged particle $p_1$, $p_2$, and $p_3$, respectively, is characterized by a single-particle spectral fingerprint spectrum, $S(p_1)$, $S(p_2)$, and $S(p_3)$, respectively, referenced by 30, 32, and 34, respectively.

In Step (c), there is identifying at least one spectral shift, preferably, a plurality of spectral shifts, in each set of the single-particle spectral fingerprint data associated with a single particle, for forming an intra-particle crystallographic region group featuring a plurality of sub-sets of intra-particle spectral fingerprint pattern data, where selected data elements in each sub-set are shifted relative to corresponding data elements in each remaining sub-set in the same intra-particle region group.

This spectral shift identification step is performed for each of the number, n, imaged particles of the substance, for forming a plurality of intra-particle region groups of sub-sets of intra-particle spectral fingerprint pattern data, relating to the entire chemically pure crystalline particulate substance 10. This data is stored in an intra-particle scenario database.

The identification procedure involves analyzing the plurality of spectral images for those particular spectral images which only 'slightly' differ by relatively small shifts in the affected energy, $E(p_i)$, and/or, only 'slightly' differ by relatively small shifts in the intensity or amplitude, $A(p_i)$, collected by spectral imaging system 14. Preferably, the identification procedure involves analyzing the plurality of spectral images for those particular spectral images which only slightly differ by relatively small shifts in the affected energy, $E(p_i)$, 20, in terms of a shift in wavelength, frequency, or, wavenumber, of fluorescent or phosphorescent light emitted by an imaged particle, $p_i$, and collected by spectral imaging system 14.

Specifically, there is identifying at least one spectral shift, $s_i$, in each set of single-particle spectral fingerprint data, $F(p_i)$, associated with an imaged particle, $p_i$, for forming an intra-particle crystallographic region group, herein, referred to as $CRG(p_i)$, featuring a plurality of sub-sets of intra-particle spectral fingerprint pattern data, herein, referred to as $FP(p_i, CR_j)$, where selected data elements, for example, affected energy, $E(p_i)$, and/or, intensity or amplitude, $A(p_i)$, in each sub-set, $FP(p_i, CR_j)$, are shifted relative to corresponding data elements in each remaining sub-set, $FP(p_i, CR_k)$, for k not equal to j, in the same intra-particle crystallographic region group, $CRG(p_i)$.

Intra-particle crystallographic region group sub-set identifier, $CR_j$, for j=1 to J different sub-sets in each intra-particle crystallographic region group, is used for distinguishing among the plurality of sub-sets of intra-particle spectral fingerprint pattern data, $FP(p_i, CR_j)$, associated with the same set of single-particle spectral fingerprint data, $F(p_i)$. This classification enables performing next Step (d) of forming a set of intra-particle crystallographic parameter data from each intra-particle crystallographic region group, $CRG(p_i)$, featuring the plurality of sub-sets of intra-particle spectral fingerprint pattern data, $FP(p_i, CR_j)$.

Each sub-set of intra-particle spectral fingerprint pattern data, $FP(p_i, CR_j)$, is characterized by an intra-particle spectral fingerprint pattern spectrum, $S(p_i, CR_j)$, featuring intensity or amplitude, $A(p_i, CR_j)$, plotted as a function of affected energy, $E(p_i, CR_j)$, 20 collected during imaging particle, $p_i$, by spectral imaging system 14. This data is stored in an intra-particle scenario database.

Figure 2:
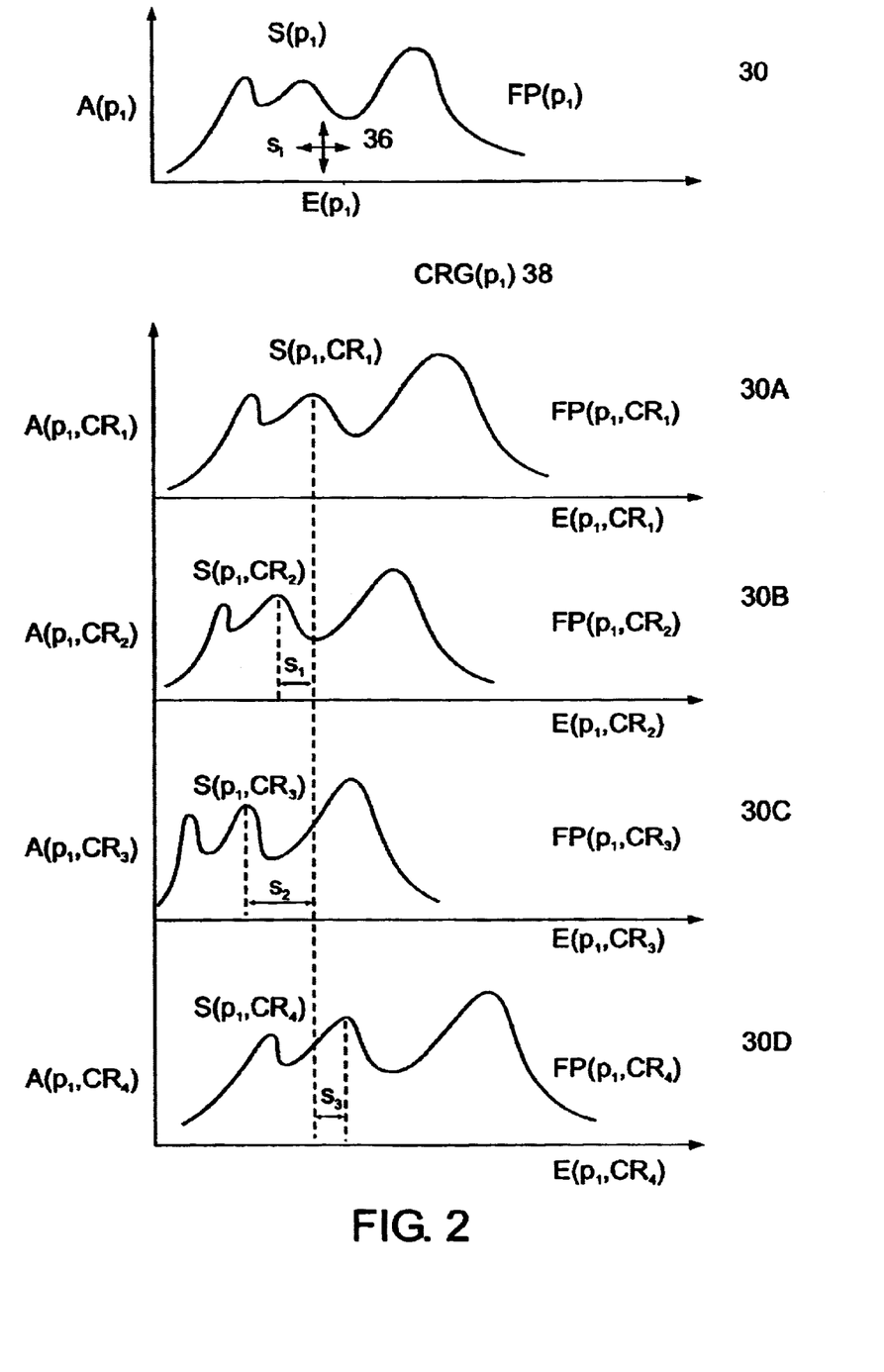
FIG. 2 is a schematic diagram illustrating the step of identifying spectral shifts in intra-particle spectral imaging data, in general, and in focus-fusion multi-layer spectral imaging data, in particular, in accordance with the present invention.

The above described process of identifying spectral shifts is clearly illustrated in FIG. 2, a schematic diagram illustrating the step of identifying spectral shifts in intra-particle spectral imaging data, in general, and in focus-fusion multi-layer spectral imaging data, in particular. For example, in the set of single-particle spectral fingerprint data, $F(p_i)$, 30 (from FIG. 1) associated with imaged particle, $p_i$, and characterized by single-particle spectral fingerprint spectrum, $S(p_i)$, there is identifying at least one spectral shift, $s_i$, of selected data elements, for example, affected energy, $E(p_i)$, and/or, intensity or amplitude, $A(p_i)$, where such potentially identified spectral shifts, $s_i$, are referenced in FIG. 2 by the four directional crossed arrows 36, for forming intra-particle crystallographic region group, $CRG(p_i)$ 38. In this example, for imaged particle $p_i$, $CRG(p_i)$ 38 features four sub-sets of intra-particle spectral fingerprint pattern data, $FP(p_1, CR_1)$, $FP(p_1, CR_2)$, $FP(p_1, CR_3)$, and $FP(p_1, CR_4)$, where each sub-set is characterized by a corresponding intra-particle spectral fingerprint pattern spectrum, $S(p_1, CR_1)$, $S(p_1, CR_2)$, $S(p_1, CR_3)$, and $S(p_1, CR_4)$, respectively, referenced by 30A, 30B, 30C, and 30D, respectively.

In FIG. 2, three spectral shifts, $s_1$, $s_2$, and $s_3$, are shown identified, whereby selected data elements, for example, $E(p_i, CR_j)$, in each sub-set, $FP(p_i, CR_j)$, are shifted relative to corresponding data elements, $E(p_i, CR_k)$, in each remaining sub-set, $FP(p_i, CR_k)$, for k not equal to j, in the same intra-particle crystallographic region group, $CRG(p_i)$ 38. In this particular exemplary illustration, the first sub-set of intra-particle spectral fingerprint pattern data, $FP(p_1, CR_1)$, characterized by the corresponding intra-particle spectral fingerprint pattern spectrum, $S(p_1, CR_1)$, referenced by 30A, is shown as a baseline used in identifying and illustrating the three spectral shifts, $s_1$, $s_2$, and $s_3$, of selected data elements, in this case, $E(p_1, CR_1)$, from corresponding data elements, in this case, $E(p_1, CR_2)$, $E(p_1, CR_3)$, and $E(p_1, CR_4)$, respectively, in the three remaining sub-sets of intra-particle spectral fingerprint pattern data, $FP(p_1, CR_2)$, $FP(p_1, CR_3)$, and $FP(p_1, CR_4)$, respectively, where each remaining sub-set is characterized by the corresponding intra-particle spectral fingerprint pattern spectrum, $S(p_1, CR_2)$, $S(p_1, CR_3)$, and $S(p_1, CR_4)$, respectively, referenced by 30B, 30C, and 30D, respectively.

In Step (d), there is forming a set of intra-particle crystallographic parameter data, relating to each imaged particle of the chemically pure crystalline particulate substance, from each intra-particle crystallographic region group featuring the plurality of sub-sets of intra-particle spectral fingerprint pattern data associated with a corresponding set of single-particle spectral fingerprint data.

For each imaged particle, the set of intra-particle crystallographic parameter data features a plurality of intra-particle crystallographic region types, where each intra-particle crystallographic region type is associated with a crystal type and a crystal class of the chemically pure crystalline particulate substance. This step is performed for each of the number, n, imaged particles of the particulate substance, for forming a plurality of sets of intra-particle crystallographic parameter data, relating to and characterizing the entire chemically pure crystalline particulate substance 10. This data is stored in an intra-particle crystallographic parameter database.

Specifically, each imaged particle, $p_i$, of chemically pure crystalline particulate substance 10 being analyzed is considered morphologically heterogeneous, and features a plurality of intra-particle crystallographic region types, $CR_j$, for j=1 to J different types of intra-particle crystallographic regions identified in, or assigned to, a particle, corresponding to the intra-particle crystallographic region group sub-set identifier, $CR_j$, used in Step (c) for distinguishing among the plurality of sub-sets of intra-particle spectral fingerprint pattern data, $FP(p_i, CR_j)$, associated with the same set of single-particle spectral fingerprint data, $F(p_i)$, as shown in FIG. 2.

Figure 3:
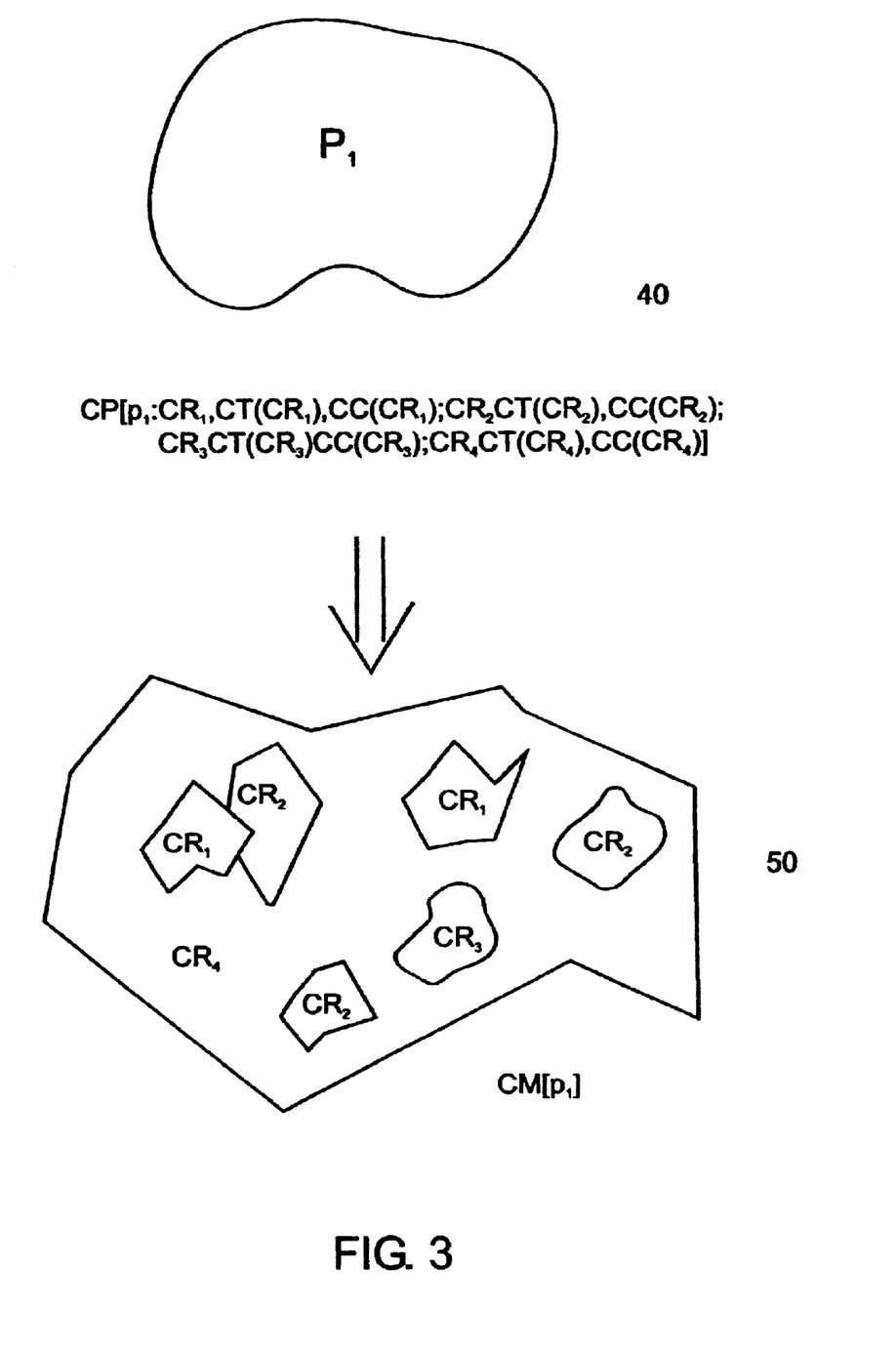
FIG. 3 is a schematic diagram illustrating an intra-particle crystallographic parameter map of a particle, generated from the exemplary set of intra-particle crystallographic parameter data formed from the results of FIG. 2, in accordance with the present invention.

FIG. 3 is a schematic diagram illustrating an intra-particle crystallographic parameter map of a particle, generated from the exemplary set of intra-particle crystallographic parameter data formed from the results of FIG. 2, for imaged particle, $p_i$. Each intra-particle crystallographic region type, $CR_j$, is associated with a crystal type, herein, referred to as $CT(CR_j)$, and a crystal class, herein, referred to as $CC(CR_j)$, of the chemically pure substance making up each imaged particle, $p_i$, where $CT(CR_j)$, and $CC(CR_j)$ vary throughout each imaged particle, $p_i$. Due to the local, intra-particle, variation, heterogeneity, or fluctuation in morphological or geometrical distribution, and subsequently, frequency distribution, of particle crystallographic parameters such as crystal type and crystal class, and due to local, intra-particle, variation or heterogeneity in surface concentration and/or density of the chemically pure substance of imaged particle, $p_i$, the incident energy 16 (FIG. 1) is affected differently by each intra-particle crystallographic region type, $CR_j$.

This intra-particle physicochemical phenomenon existing during imaging particles of chemically pure crystalline particulate substance 10, enables forming intra-particle crystallographic region group, $CRG(p_i)$, in Step (c), featuring the plurality of sub-sets of intra-particle spectral fingerprint pattern data, $FP(p_i, CR_j)$, where selected data elements in each sub-set $FP(p_i, CR_j)$, are shifted relative to corresponding data elements in each remaining sub-set, $FP(p_i, CR_k)$, for k not equal to j, in the same intra-particle crystallographic region group, $CRG(p_i)$, as illustratively exemplified in FIG. 2.

Pattern recognition and classification of the crystal type, $CT(R_j)$, and the crystal class, $CC(CR_j)$, are performed by relating the spectral imaging data, in general, and by relating the focus-fusion multi-layer spectral imaging data, in particular, in each intra-particle crystallographic region group, $CRG(p_i)$ (FIG. 2), obtained and stored from imaging the sample of chemically pure crystalline particulate substance, to empirically determined spectral imaging data in a standard intra-particle crystallographic region group, herein, referred to as $CRG(p_i)^s$, obtained and stored from imaging a calibration or standard sample of a chemically pure crystalline particulate substance featuring known local, intra-particle, variation or heterogeneity in particle crystallographic parameters such as crystal type and crystal class, and known local, intra-particle, variation or heterogeneity in surface concentration and/or density of the chemically pure crystalline particulate substance of the standard sample.

Accordingly, for each imaged particle, $p_i$, the set of intra-particle crystallographic parameter data is referred to as $CP[p_i:CR_j, CT(CR_j), CC(CR_j)]$, for j=1 to J different types of intra-particle crystallographic regions. For example, for imaged particle $p_i$, the set of intra-particle crystallographic parameter data is written as: $CP[p_i:CR_j, CT(CR_j), CC(CR_j)]$, for j=1 to 4. $CT(CR_j)$ and $CC(CR_j)$, for j=1 to 4, are evaluated from the four sub-sets of intra-particle spectral fingerprint pattern data, $FP(p_1, CR_1)$, $FP(p_1, CR_2)$, $FP(p_1, CR_3)$, and $FP(p_1, CR_4)$, respectively, where each sub-set is characterized by the corresponding intra-particle spectral fingerprint pattern spectrum, $S(p_1, CR_1)$, $S(p_1, CR_2)$, $S(p_1, CR_3)$, and $S(p_1, CR_4)$, respectively, and associated with four corresponding different intra-particle crystallographic region types, $CR_1$, $CR_2$, $CR_3$, and $CR_4$. Thus, as shown in FIG. 3, for exemplary imaged particle, $p_i$, the complete set of intra-particle crystallographic parameter data becomes: $CP[p_1:CR_1, CT(CR_1), CC(CR_1); CR_2, CT(CR_2), CC(CR_2); CR_3, CT(CR_3), CC(CR_3); CR_4, CT(CR_4), CC(CR_4)]$, referenced by 40.

In Step (e), there is generating an intra-particle crystallographic parameter map from each set of intra-particle crystallographic parameter data, for illustrating local, intra-particle, morphological or geometrical distribution of crystal type and crystal class of the chemically pure crystalline substance throughout the particle associated with that set of intra-particle crystallographic parameter data.

This step is performed for each of a number, n, imaged particles of the substance, for generating n crystallographic parameter maps, relating to the chemically pure crystalline particulate substance 10. Each crystallographic parameter map is stored in an intra-particle crystallographic parameter map database.

Specifically, for each imaged particle, $p_i$, of chemically pure particulate substance 10 being analyzed, there is generating an intra-particle crystallographic parameter map, $CM[p_i]$, from each set of intra-particle crystallographic parameter data, $CP[p_i:CR_j, CT(CR_j), CC(CR_j)]$, for j=1 to J, featuring J different types of intra-particle crystallographic regions, where each intra-particle crystallographic region type, $CR_j$, is associated with a crystal type, $CT(CR_j)$, and a crystal class, $CC(CR_j)$, of the chemically pure crystalline particulate substance.

For example, referring again to FIG. 3, for imaged particle, $p_i$, having the set of intra-particle crystallographic parameter data, $CP[p_1:CR_1, CT(CR_1), CC(CR_1); CR_2, CT(CR_2), CC(CR_2); CR_3, CT(CR_3), CC(CR_3); CR_4, CT(CR_4), CC(CR_4)]$ 40, which is formed and has assigned values according to previously described Step (d) above, there is generating intra-particle crystallographic parameter map, $CM[p_i]$ 50. As illustrated, intra-particle crystallographic parameter map, $CM[p_i]$ 50, features a heterogeneous distribution of four different intra-particle crystallographic region types, $CR_1$, $CR_2$, $CR_3$, and $CR_4$, where each intra-particle crystallographic region type, $CR_j$, is associated with a crystal type, $CT(CR_j)$, and a crystal class, $CC(CR_j)$, of the chemically pure crystalline particulate substance. As previously described above, this heterogeneous distribution of four different intra-particle crystallographic region types, $CR_j$, is due to local, intra-particle, variation, heterogeneity, or fluctuation in morphological or geometrical distribution, and subsequently, frequency distribution, of particle crystallographic parameters such as crystal type and crystal class, and due to local, intra-particle, variation or heterogeneity in surface concentration and/or density of the chemically pure substance of imaged particle, $p_i$, whereby the incident energy 16 (FIG. 1) is affected differently by each intra-particle crystallographic region type, $CR_j$.

In Step (f), there is generating a crystallographic parameter histogram, or frequency distribution, from the plurality of sets of the intra-particle crystallographic parameter data, for illustrating a statistically based global morphological or geometrical frequency distribution of crystallographic parameters of the chemically pure crystalline substance throughout the entire chemically pure crystalline particulate sample.

This step is performed using the previously obtained data sets of the number, n, imaged particles of the substance, for generating the crystallographic parameter histogram, or frequency distribution, relating to and representative of the entire chemically pure crystalline particulate substance 10. Each histogram is stored in a crystallographic parameter histogram database.

Specifically, using the previously obtained data sets of the n imaged particles, $p_i$, for i=1 to n, making up sample number, $(sample)_n$, of chemically pure crystalline particulate substance 10 being analyzed, there is generating a crystallographic parameter histogram, herein, referred to as $CH[(sample)_n]$, from the plurality of sets of intra-particle crystallographic parameter data, $CP[p_i:CR_j, CT(CR_j), CC(CR_j)]$, for i=1 to n, and j=1 to J, for each particle number, i, and for J different types of intra-particle crystallographic regions, $CR_j$, where J can vary among the imaged particles.

Figure 4:
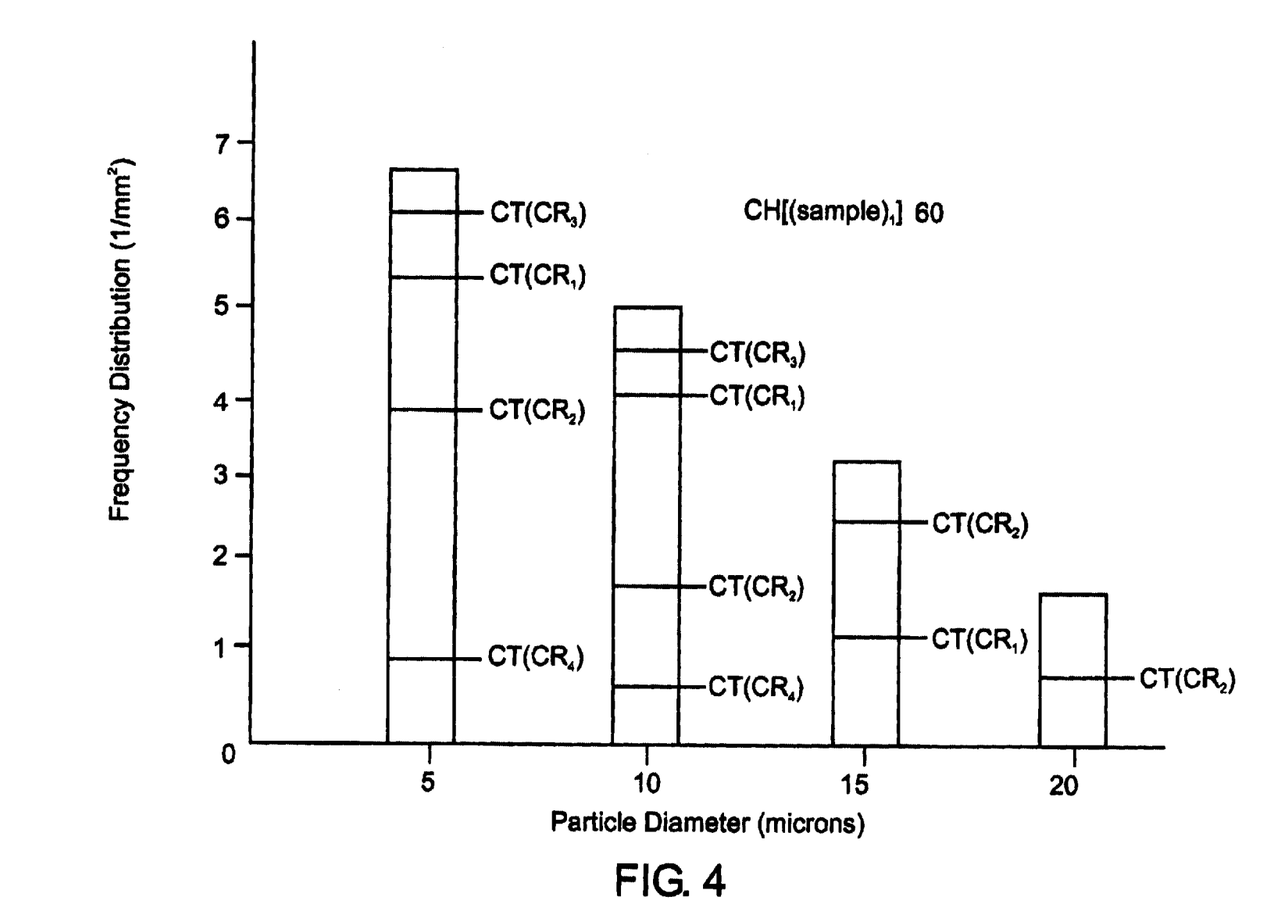
FIG. 4 is a schematic diagram illustrating a crystallographic parameter histogram generated from a plurality of sets of intra-particle crystallographic parameter map data, corresponding to a statistically based global morphological or geometrical frequency distribution of the crystallographic parameters of the chemically pure crystalline particulate substance throughout the entire multi-particle sample, in accordance with the present invention.

For example, referring to FIG. 4, a schematic diagram illustrating a crystallographic parameter histogram generated from a plurality of sets of intra-particle crystallographic parameter map data, from the data sets of the n imaged particles of $(sample)_1$ representative of chemically pure crystalline particulate substance 10. Crystallographic parameter histogram, $CH[(sample)_1]$ 60, is generated from the plurality of sets of intra-particle crystallographic parameter data, $CP[p_i:CR_j, CT(CR_j), CC(CR_j)]$, for i=1 to n, and j=1 to J, for each particle number, i, corresponding to a statistical morphological or geometrical frequency distribution of the crystallographic parameters of crystal type, $CT(CR_j)$, and crystal class, $CC(CR_j)$, of a plurality of individual particles of chemically pure crystalline particulate substance 10.

In the example illustrated in FIG. 4, crystallographic parameter histogram, $CH[(sample)_1]$ 60, features a graphical plot of the statistical frequency distribution of the crystallographic parameter, crystal type, $CT(CR_j)$, of the chemically pure crystalline particulate substance in each intra-particle crystallographic region type, $CR_j$, as a function of particle diameter (microns), among the plurality of particles of substance 10. For illustrative purposes, four intra-particle crystallographic region types, $CR_1$, $CR_2$, $CR_3$, and $CR_4$, each associated with a corresponding intra-particle crystal type, $CT(CR_1)$, $CT(CR_2)$, $CT(CR_3)$, and $CT(CR_4)$, respectively, are shown in crystallographic parameter histogram, $CH[(sample)_1]$ 60.

Although not particularly shown in FIG. 4, the same plurality of sets of intra-particle crystallographic parameter data, $CP[p_i:CR_j, CT(CR_j), CC(CR_j)]$, for i=1 to n, and j=1 to J, for each particle number, i, is used for generating another crystallographic parameter histogram, $CH[(sample)_1]$, featuring a graphical plot of the statistical frequency distribution of the crystallographic parameter, crystal class, $CC(CR_j)$, instead of the crystal type, $CT(CR_j)$, of the chemically pure crystalline particulate substance in each intra-particle crystallographic region type, $CR_j$, as a function of particle diameter (microns), among the plurality of particles of substance 10.

The method of the present invention is applicable to a variety of industries, such as the biopharmaceutical, food, and beverage, industries, currently devoting significant amounts of resources towards better measurement, analysis, understanding, and application, of crystallographic data, information, and parameters, of chemically pure crystalline particulate substances in the form of raw materials and/or finished products. The method of the present invention is particularly applicable to those sectors of the biopharmaceutical industry currently or considering developing, testing, and manufacturing, pharmaceutical products which include chemically pure crystalline particulate substances featuring different isomers and/or polymorphs exhibiting significantly different physicochemical properties and characteristics that are a function of crystallographic parameters of crystal type and crystal class, giving rise to significantly different behavior, efficacy, and therapeutic effects, when subjected to the same laboratory in-vitro conditions and/or clinical in-vivo conditions.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for generating intra-particle crystallographic parameter maps and histograms of a chemically pure crystalline particulate substance, comprising the steps of:
   (a) acquiring a set of spectral images by a spectral imaging system for each of a number of particles of the chemically pure crystalline particulate substance having a plurality of said particles;
   (b) performing pattern recognition classification analysis on each said set of said acquired spectral images for each said imaged particle, for forming a number of sets of single-particle spectral fingerprint data;
   (c) identifying at least one spectral shift in each said set of single-particle spectral fingerprint data associated with each said imaged particle, for forming an intra-particle crystallographic region group featuring a plurality of sub-sets of intra-particle spectral fingerprint pattern data, where selected data elements in each said sub-set are shifted relative to corresponding said data elements in each remaining said sub-set in same said intra-particle crystallographic region group;
   (d) forming a set of intra-particle crystallographic parameter data relating to each said imaged particle from each said intra-particle crystallographic region group;
   (e) generating each of the intra-particle crystallographic parameter maps from each said set of said intra-particle crystallographic parameter data; and
   (f) generating each of the crystallographic parameter histograms from a plurality of said sets of said intra-particle crystallographic parameter data, for illustrating a statistically based global morphological or geometrical frequency distribution of crystallographic parameters of the chemically pure particulate crystalline substance throughout the chemically pure crystalline particulate substance.

2. The method of claim 1, whereby the chemically pure crystalline particulate substance is a crystalline particulate substance comprising a plurality of crystalline particles each composed of at least one chemically pure individual chemical compound.

3. The method of claim 2, whereby said at least one chemically pure individual chemical compound exhibits isomerism, and comprises a number of isomers.

4. The method of claim 2, whereby said at least one chemically pure individual chemical compound exhibits polymorphism, and comprises a number of polymorphs.

5. The method of claim 2, whereby the chemically pure crystalline particulate substance is heterogeneous with respect to morphological or geometrical distribution of crystallographic parameters of crystal type and crystal class, of said at least one chemically pure individual compound throughout a sample of the chemically pure crystalline particulate substance.

6. The method of claim 1, whereby physicochemical properties and characteristics of the chemically pure crystalline particulate substance are selected from the group consisting of independent of particle depth and dependent of particle depth.

7. The method of claim 1, whereby the chemically pure crystalline particulate substance is selected from the group consisting of a separate stand alone powdered entity or substance, and a powdered entity or substance part of another entity or substance in a solid or liquid phase having a function selected from the group consisting of as a substrate of, containing, hosting, delivering, receiving, and combinations thereof, the chemically pure crystalline particulate substance.

8. The method of claim 1, whereby the chemically pure crystalline particulate substance is a powder in a form selected from the group consisting of a powder and a powder mixture.

9. The method of claim 8, whereby said powder is in a configuration or form selected from the group consisting of loose or free flowing, packed, compacted, and combinations thereof.

10. The method of claim 8, whereby said powder is composed of components selected from the group consisting of inorganic components, organic components, and combinations thereof.

11. The method of claim 8, whereby said powder is of origin or derivation selected from the group consisting of natural origin or derivation, synthetic origin or derivation, and combinations thereof.

12. The method of claim 1, whereby the chemically pure crystalline particulate substance is a raw material used in manufacturing a product selected from the group consisting of a pharmaceutical product, a food product, and a beverage product.

13. The method of claim 1, whereby the chemically pure crystalline particulate substance is selected from the group consisting of a medicinal or therapeutic powder, a high performance powdered chemical, and a powdered biological specimen.

14. The method of claim 13, whereby said medicinal or therapeutic powder is part of a pharmaceutical product in a form selected from the group consisting of a tablet, a capsule, a caplet, a loose powder, a gel, a liquid suspension, and a liquid solution.

15. The method of claim 1, wherein step (a) said spectral images are focus-fusion multi-layer spectral images acquired by focus-fusion multi-layer spectral imaging of said particles of the chemically pure crystalline particulate substance.

16. The method of claim 1, wherein step (a) said spectral imaging system includes an imaging energy source supplying imaging source energy incident upon the chemically pure crystalline particulate substance, said imaging source energy is affected by said imaged particles by at least one mechanism selected from the group consisting of absorption, reflection, transmission, diffraction, scattering, fluorescence, and phosphorescence.

17. The method of claim 1, whereby each said set of single-particle spectral fingerprint data is characterized by a single-particle spectral fingerprint spectrum featuring intensity or amplitude plotted as a function of incident imaging energy affected by a said imaged particle and collected during imaging said particle by said spectral imaging system.

18. The method of claim 17, whereby said affected energy is expressed in a term selected from the group consisting of wavelength, frequency, and, wavenumber, of electromagnetic radiation emitted by said imaged particle.

19. The method of claim 1, wherein step (c) said identifying said at least one spectral shift is performed for each said imaged particle of the chemically pure crystalline particulate substance, for forming a plurality of said intra-particle crystallographic region groups of said sub-sets of said intra-particle spectral fingerprint pattern data relating to the entire chemically pure particulate substance.

20. The method of claim 1, wherein step (c) said selected data elements of said sub-sets of said intra-particle spectral fingerprint pattern data are selected from the group consisting of incident imaging energy affected by a said imaged particle and intensity or amplitude of said incident imaging energy affected by said imaged particle.

21. The method of claim 1, wherein step (c) said selected data elements of said sub-sets of said intra-particle spectral fingerprint pattern data are incident imaging energy affected by a said imaged particle.

22. The method of claim 1, wherein step (c) each said sub-set of said intra-particle spectral fingerprint pattern data is characterized by an intra-particle spectral fingerprint pattern spectrum featuring intensity or amplitude plotted as a function of incident imaging energy affected by a said imaged particle.

23. The method of claim 1, wherein step (d) said set of said intra-particle crystallographic parameter data features a plurality of intra-particle crystallographic region types.

24. The method of claim 23, whereby each said intra-particle crystallographic region type is associated with a crystal type and a crystal class of the chemically pure crystalline particulate substance.

25. The method of claim 1, wherein step (e) each said crystallographic parameter map illustrates local, intra-particle, morphological or geometrical distribution of a plurality of crystallographic region types each associated with crystal types and crystal classes of the chemically pure crystalline substance throughout a said imaged particle.

26. The method of claim 1, wherein step (f) said crystallographic parameters in a said crystallographic parameter histogram are selected from the group consisting of crystal type, crystal class, and combinations thereof.

27. A method for identifying and illustrating intra-particle morphological or geometrical distribution of crystallographic parameters of a chemically pure crystalline particulate substance, comprising the steps of:

(a) acquiring a set of spectral images by a spectral imaging system for each of a number of particles of the chemically pure crystalline particulate substance having a plurality of said particles;

(b) performing pattern recognition classification analysis on each said set of said acquired spectral images for each said imaged particle, for forming a number of sets of single-particle spectral fingerprint data;

(c) identifying at least one spectral shift in each said set of single-particle spectral fingerprint data associated with each said imaged particle, for forming an intra-particle crystallographic region group featuring a plurality of sub-sets of intra-particle spectral fingerprint pattern data, where selected data elements in each said sub-set are shifted relative to corresponding said data elements in each remaining said sub-set in same said intra-particle crystallographic region group;

(d) forming a set of intra-particle crystallographic parameter data relating to each said imaged particle from each said intra-particle crystallographic region group; and (e) generating a plurality of intra-particle crystallographic parameter maps and histograms from a plurality of said sets of said intra-particle crystallographic parameter data, for identifying and illustrating the intra-particle morphological or geometrical distribution of the crystallographic parameters of the chemically pure particulate crystalline substance throughout the chemically pure crystalline particulate substance.

28. The method of claim 27, whereby the chemically pure crystalline particulate substance is a crystalline particulate substance comprising a plurality of crystalline particles each composed of at least one chemically pure individual chemical compound.

29. The method of claim 28, whereby said at least one chemically pure individual chemical compound exhibits isomerism, and comprises a number of isomers.

30. The method of claim 28, whereby said at least one chemically pure individual chemical compound exhibits polymorphism, and comprises a number of polymorphs.

31. The method of claim 28, whereby the chemically pure crystalline particulate substance is heterogeneous with respect to morphological or geometrical distribution of crystallographic parameters of crystal type and crystal class, of said at least one chemically pure individual compound throughout a sample of the chemically pure crystalline particulate substance.

32. The method of claim 27, whereby physicochemical properties and characteristics of the chemically pure crystalline particulate substance are selected from the group consisting of independent of particle depth and dependent of particle depth.

33. The method of claim 27, whereby the chemically pure crystalline particulate substance is selected from the group consisting of a separate stand alone powdered entity or substance, and a powdered entity or substance part of another entity or substance in a solid or liquid phase having a function selected from the group consisting of as a substrate of, containing, hosting, delivering, receiving, and combinations thereof, the chemically pure crystalline particulate substance.

34. The method of claim 27, whereby the chemically pure crystalline particulate substance is a powder in a form selected from the group consisting of a powder and a powder mixture.

35. The method of claim 34, whereby said powder is in a configuration or form selected from the group consisting of loose or free flowing, packed, compacted, and combinations thereof.

36. The method of claim 34, whereby said powder is composed of components selected from the group consisting of inorganic components, organic components, and combinations thereof.

37. The method of claim 34, whereby said powder is of origin or derivation selected from the group consisting of natural origin or derivation, synthetic origin or derivation, and combinations thereof.

38. The method of claim 27, whereby the chemically pure crystalline particulate substance is a raw material used in manufacturing a product selected from the group consisting of a pharmaceutical product, a food product, and a beverage product.

39. The method of claim 27, whereby the chemically pure crystalline particulate substance is selected from the group consisting of a medicinal or therapeutic powder, a high performance powdered chemical, and a powdered biological specimen.

40. The method of claim 39, whereby said medicinal or therapeutic powder is part of a pharmaceutical product in a form selected from the group consisting of a tablet, a capsule, a caplet, a loose powder, a gel, a liquid suspension, and a liquid solution.

41. The method of claim 27, wherein step (a) said spectral images are focus-fusion multi-layer spectral images acquired by focus-fusion multi-layer spectral imaging of said particles of the chemically pure crystalline particulate substance.

42. The method of claim 27, wherein step (a) said spectral imaging system includes an imaging energy source supplying imaging source energy incident upon the chemically pure crystalline particulate substance, said imaging source energy is affected by said imaged particles by at least one mechanism selected from the group consisting of absorption, reflection, transmission, diffraction, scattering, fluorescence, and phosphorescence.

43. The method of claim 27, whereby each said set of single-particle spectral fingerprint data is characterized by a single-particle spectral fingerprint spectrum featuring intensity or amplitude plotted as a function of incident imaging energy affected by a said imaged particle and collected during imaging said particle by said spectral imaging system.

44. The method of claim 43, whereby said affected energy is expressed in a term selected from the group consisting of wavelength, frequency, and, wavenumber, of electromagnetic radiation emitted by said imaged particle.

45. The method of claim 27, wherein step (c) said identifying said at least one spectral shift is performed for each said imaged particle of the chemically pure crystalline particulate substance, for forming a plurality of said intra-particle crystallographic region groups of said sub-sets of said intra-particle spectral fingerprint pattern data relating to the entire chemically pure particulate substance.

46. The method of claim 27, wherein step (c) said selected data elements of said sub-sets of said intra-particle spectral fingerprint pattern data are selected from the group consisting of incident imaging energy affected by a said imaged particle and intensity or amplitude of said incident imaging energy affected by said imaged particle.

47. The method of claim 27, wherein step (c) said selected data elements of said sub-sets of said intra-particle spectral fingerprint pattern data are incident imaging energy affected by a said imaged particle.

48. The method of claim 27, wherein step (c) each said sub-set of said intra-particle spectral fingerprint pattern data is characterized by an intra-particle spectral fingerprint pattern spectrum featuring intensity or amplitude plotted as a function of incident imaging energy affected by a said imaged particle.

49. The method of claim 27, wherein step (d) said set of said intra-particle crystallographic parameter data features a plurality of intra-particle crystallographic region types.

50. The method of claim 49, whereby each said intra-particle crystallographic region type is associated with a crystal type and a crystal class of the chemically pure crystalline particulate substance.

51. The method of claim 27, wherein step (e) each said crystallographic parameter map illustrates local, intra-particle, morphological or geometrical distribution of a plurality of crystallographic region types each associated with crystal types and crystal classes of the chemically pure crystalline substance throughout a said imaged particle.

52. The method of claim 27, wherein step (e) the crystallographic parameters in a said crystallographic parameter histogram are selected from the group consisting of crystal type, crystal class, and combinations thereof.

* * * * *